United States Patent
Kim et al.

(10) Patent No.: US 11,214,570 B2
(45) Date of Patent: Jan. 4, 2022

(54) PYRROLOPYRIDINE DERIVATIVE, METHOD FOR PRODUCING SAME, AND USE THEREOF

(71) Applicant: ST PHARM CO., LTD., Siheung-si (KR)

(72) Inventors: Bong Jin Kim, Saejong-si (KR); Ill Young Lee, Daejeon (KR); Jae Hak Kim, Daejeon (KR); Hong Suk Shin, Jeonju-si (KR); Jong Chan Son, Chungcheongnam-do (KR); Chong-Kyo Lee, Daejeon (KR); Kyungjin Kim, Seoul (KR); Uk-Il Kim, Ansan-si (KR); Hwa Jung Nam, Busan (KR)

(73) Assignee: ST PHARM CO., LTD., Siheung-si (KR)

( * ) Notice: Subject to any disclaimer, the term of this patent is extended or adjusted under 35 U.S.C. 154(b) by 69 days.

(21) Appl. No.: 16/497,255

(22) PCT Filed: Mar. 24, 2017

(86) PCT No.: PCT/KR2017/003194
§ 371 (c)(1),
(2) Date: Sep. 24, 2019

(87) PCT Pub. No.: WO2018/174320
PCT Pub. Date: Sep. 27, 2018

(65) Prior Publication Data
US 2020/0377498 A1 Dec. 3, 2020

(51) Int. Cl.
*C07D 471/04* (2006.01)
*A61P 31/18* (2006.01)

(52) U.S. Cl.
CPC ............ *C07D 471/04* (2013.01); *A61P 31/18* (2018.01)

(58) Field of Classification Search
CPC .............................. A61P 31/18; A61K 31/437
See application file for complete search history.

(56) References Cited

U.S. PATENT DOCUMENTS

| | | | |
|---|---|---|---|
| 9,499,537 B2 * | 11/2016 | Son | ....... C07D 471/04 |
| 2014/0249162 A1 * | 9/2014 | Son | ....... A61P 31/18 |
| | | | 514/255.05 |

FOREIGN PATENT DOCUMENTS

| | | |
|---|---|---|
| KR | 10-2015-0141275 A | 12/2015 |
| WO | 2005/103003 A2 | 11/2005 |
| WO | 2013/012649 A1 | 1/2013 |
| WO | 2014/009764 A1 | 1/2014 |

OTHER PUBLICATIONS

Christ at al., "Rational design of small-molecule inhibitors of the LEDGF/p75-integrase interaction and HIV replication", Nature Chemical Biology, 2010, vol. 6, pp. 442-448.

* cited by examiner

*Primary Examiner* — D Margaret M Seaman
(74) *Attorney, Agent, or Firm* — Vorys, Sater, Seymour and Pease LLP; Mih Suhn Koh

(57) ABSTRACT

Provided is a novel pyrrolopyridine compound represented by Chemical Formula I, a racemate or a stereoisomer thereof, or a pharmaceutically acceptable salt thereof; and to a method for preparing the same. A compound represented by Chemical Formula I shows high selectivity and antiviral activity against human immunodeficiency virus (HIV), with low toxicity; therefore, it is useful as a therapeutic agent for viral infection, in particular, HIV infection.

3 Claims, No Drawings

PYRROLOPYRIDINE DERIVATIVE, METHOD FOR PRODUCING SAME, AND USE THEREOF

TECHNICAL FIELD

The present invention relates to an antiviral compound, more particularly, a compound exhibiting high selectivity and physiological activity against human immunodeficiency virus (HIV), to a method for preparing the same, and to the use thereof.

BACKGROUND ART

Acquired immune deficiency syndrome (AIDS) is caused by human immunodeficiency virus (HIV) infection. There are two types of HIVs, HIV-1 and HIV-2, and the type most prevalent globally is HIV-1. For the treatment of AIDS, enzyme inhibitors have been developed in accordance with action mechanisms of HIV. Depending on the point of action, those inhibitors are classified into Nucleoside Reverse Transcriptase Inhibitor (NRTI), Protease Inhibitor (PI), Fusion Inhibitor, and Integrase Inhibitor.

Integrase Inhibitors are classified into catalytic site inhibitors and non-catalytic site inhibitors. Research on the catalytic site integrase inhibitors have been actively conducted to date, and three kinds of drugs have been developed and are commercially available. Raltegravir, developed in 2008, is a representative drug. Meanwhile, the action mechanism of the non-catalytic site integrase inhibitors was introduced by Ziger Debyser, et al. (Frauke Christ, Zeger Debyser et al., Nature Chemical Biology, 2010, Vol. 6, 442), and development of inhibitors for this action mechanism has been actively proceeded.

In addition, a variety of studies have been conducted to develop drugs for effectively treating against resistant viruses. Such chemotherapeutic agents are administrated in combination of two or four drugs that inhibit different mechanisms of action, which are referred to as Highly Active Anti-Retroviral Therapies (HAART), thereby resulting in great life extension effects. Despite such efforts, however, AIDS has not been completely cured, and due to drug toxicity and expression of resistance to current therapeutic agents, the development of new drugs is being required continually.

DISCLOSURE OF INVENTION

Technical Problem to be Solved

In an effort to solve the above-mentioned problems, the present inventors have conducted intensive studies for searching new AIDS therapeutic agents, and as a result, found that pyrrolopyridine compounds having a novel skeleton have inhibitory effects of the proliferation of HIV. The present invention has been completed on the basis of such findings.

Therefore, one object of the present invention is to provide a novel pyrrolopyridine compound and a pharmaceutically acceptable salt thereof, which exhibits inhibitory effects of HIV-1 proliferation by inhibiting the activity of integrase enzymes of HIV-1, and also exhibits excellent results in drug property and basic toxicity tests.

Another object of the present invention is to provide a method for preparing the novel pyrrolopyridine compound as described above, and a pharmaceutically acceptable salt thereof.

A further object of the present invention is to provide a pharmaceutical composition comprising the aforementioned compound as an active ingredient.

Technical Solution

A first aspect of the present invention provides a compound represented by the following Chemical Formula I, a racemate or a stereoisomer thereof, or a pharmaceutically acceptable salt thereof:

Chemical Formula I

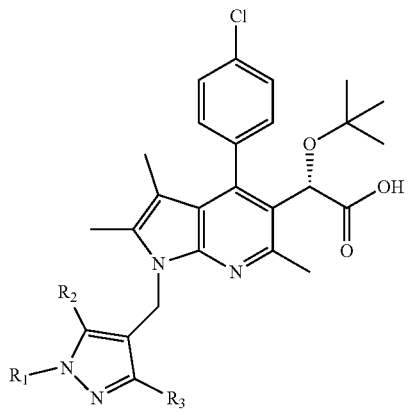

wherein, $R_1$ is selected from the group consisting of a $C_{1-6}$ alkyl unsubstituted or substituted with a halogen atom, a benzyl unsubstituted or substituted with $C_{1-3}$ alkyl or halogen, a $C_{1-3}$ alkyloxymethyl, a $C_{1-3}$ alkyl carbamate, and a sulfonyl unsubstituted or substituted with a $C_{1-3}$ alkyl, and $R_2$ and $R_3$ are each independently hydrogen, a $C_{1-6}$ alkyl, or a halogen atom.

In one embodiment, the present invention provides the compound where $R_1$ is a $C_{1-6}$ alkyl, a racemate or a stereoisomer thereof, or a pharmaceutically acceptable salt thereof.

In another embodiment, the present invention provides the compound where $R_1$ is methyl, and $R_2$ and $R_3$ are each independently hydrogen, methyl or chloro, a racemate or a stereoisomer thereof, or a pharmaceutically acceptable salt thereof.

In still another embodiment, the present invention provides the compound where $R_1$ is methyl, and both $R_2$ and $R_3$ are hydrogen, a racemate of a stereoisomer thereof, or a pharmaceutically acceptable salt thereof.

Specifically, the halogen atom refers to a chlorine, bromine or fluorine atom.

A second aspect of the present invention provides a method for preparing the compound of Chemical Formula I in accordance with Reaction Scheme 1 below:

Reaction Scheme 1

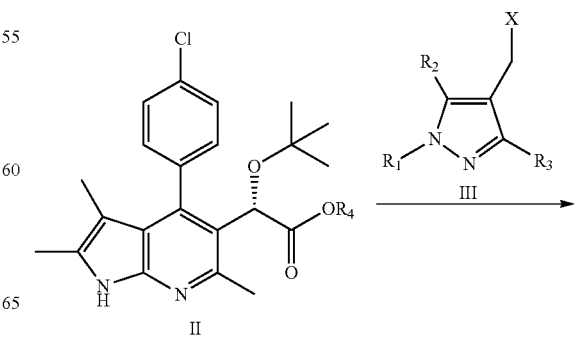

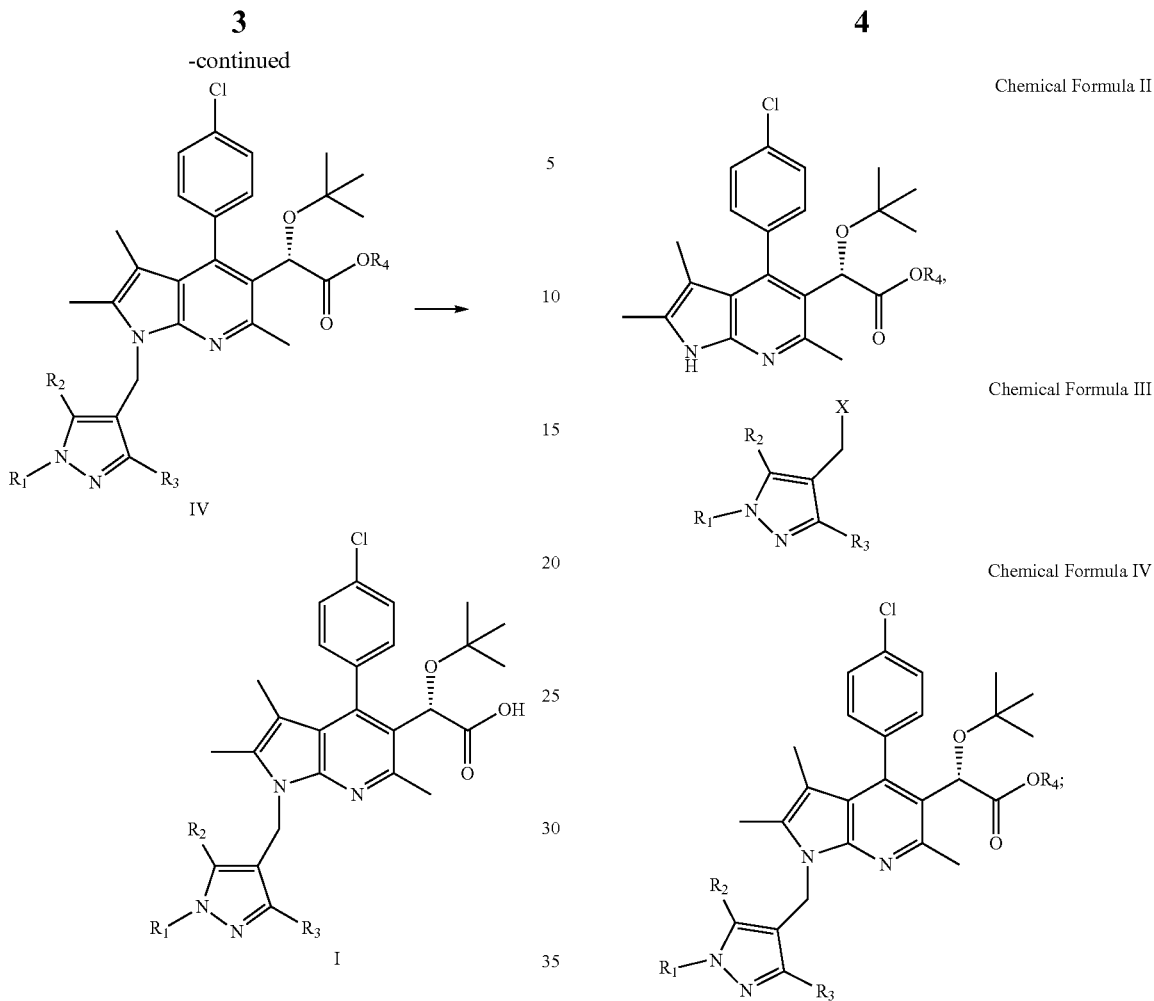

Specifically, the method for preparing the compound of Chemical Formula I,

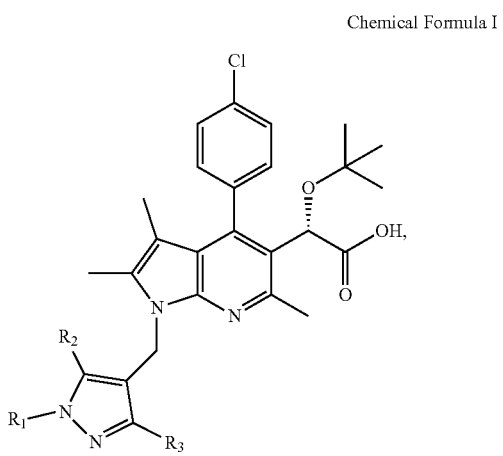

comprises:

1) first step of reacting a compound represented by Chemical Formula II with a compound represented by Chemical Formula III to prepare a compound represented by Chemical Formula IV, and 2) second step of hydrolyzing the compound represented by Chemical Formula IV, wherein, $R_1$ is selected from the group consisting of a $C_{1-6}$ alkyl unsubstituted or substituted with a halogen atom, a benzyl unsubstituted or substituted with $C_{1-3}$ alkyl or halogen atom, a $C_{1-3}$ alkyloxymethyl, a $C_{1-3}$ alkyl carbamate, and a sulfonyl unsubstituted or substituted with a $C_{1-3}$ alkyl, $R_2$ and $R_3$ are each independently hydrogen, a $C_{1-6}$ alkyl, or a halogen atom, $R_4$ is a $C_{1-6}$ alkyl, and X is halo, methanesulfonyl, toluenesulfonyl or trifluoromethanesulfonyl.

Specifically, $R_4$ may be methyl or ethyl, and X may be chloro or p-toluensufonyl.

In the first step of the method for preparing the compound of Chemical Formula I, a molar ratio between the compound of Chemical Formula II and the compound of Chemical Formula III is preferably 1:2 to 1:5, but is not limited thereto.

In the first step, a reaction solvent may be dichloromethane, dimethylformamide, tetrahydrofuran, or any combination thereof, but is not limited thereto.

The first step may be carried out for 2 hours to 18 hours, but is not limited thereto.

The first step may be carried out in the presence of cesium carbonate, and dimethylformamide is preferably used as a solvent.

In the first step, cesium carbonate is used in an amount preferably of 2 to 5 equivalents relative to the compound of Chemical Formula II.

At this time, but not limited thereto, the reaction temperature is preferably 40° C. to 100° C., and the reaction time is preferably 4 hours to 18 hours.

For example, the compound represented by Chemical Formula II, which is used as a starting material for the preparation of the compound of Chemical Formula I according to the present invention, can be prepared in accordance with the method disclosed in the preparation example of WO 2013/073875A1.

In the second step, hydrolysis may be carried out with lithium hydroxide, calcium hydroxide, barium hydroxide or potassium hydroxide, but is not limited thereto. Preferably, potassium hydroxide or lithium hydroxide may be used.

In the hydrolysis, potassium hydroxide or lithium hydroxide may be used 3 to 8 equivalents relative to the compound of Chemical Formula IV, but is not limited thereto.

The hydrolysis in the second step may be carried out at room temperature, or alternatively at 35° C. to 50° C.

In the hydrolysis, water, methanol, tetrahydrofuran or any combination thereof may be used as a solvent, but not limited thereto.

In one embodiment, the hydrolysis is carried out with lithium hydroxide in a mixed solvent, for example, 4N sodium hydroxide/methanol, or tetrahydrofuran/methanol/water.

The hydrolysis may be specifically carried out for 6 hours to 18 hours, but is not limited thereto.

A third aspect of the present invention provides an antiviral composition comprising the compound represented by Chemical Formula I described above, a racemate or a stereoisomer thereof, or a pharmaceutically acceptable salt thereof.

In particular, the above-mentioned composition is a composition for anti-human immunodeficiency virus (HIV).

In the present invention, the specific example of the compound of Chemical Formula I may be (S)-2-(tert-butoxy)-2-(4-(4-chlorophenyl)-2,3,6-trimethyl-1-((1-methyl-1H-pyrazol-4-yl)methyl)-1H-pyrrolo[2,3-b]pyridin-5-yl) acetic acid, or (S)-2-(tert-butoxy)-2-(1-((5-chloro-1,3-dimethyl-1H-pyrazol-4-yl)methyl)-4-(4-chlorophenyl)-2,3,6-trimethyl-1H-pyrrolo[2,3-b]pyridin-5-yl)acetic acid.

The compound of Chemical Formula I of the present invention prepared as above may form a salt, in particular, a pharmaceutically acceptable salt. The suitable pharmaceutically acceptable salt is not particularly limited as long as it is a salt typically used in the art, such as an acid addition salt (Refer to J. Pharm. Sci., 1977, 66, 1).

Preferable example of an acid for the pharmaceutically acceptable acid addition salt includes an inorganic acid such as hydrochloric acid, hydrobromic acid, phosphoric acid, orthophosphoric acid or sulfuric acid; or an organic acid such as methanesulfonic acid, benzenesulfonic acid, toluenesulfonic acid, acetic acid, propionic acid, lactic acid, citric acid, fumaric acid, malic acid, succinic acid, salicylic acid, maleic acid, glycerophosphoric acid or acetylsalicylic acid.

A pharmaceutically acceptable metal salt may also be obtained in accordance with a conventional method with a base. For example, a compound of Chemical Formula I may be dissolved in an excess amount of a solution of alkali metal hydroxide or alkaline earth metal hydroxide, undissolved salt of the compound may be filtered, and filtrate may then be evaporated and dried, to obtain a pharmaceutically acceptable metal salt of the compound.

A pharmaceutically unacceptable salt or solvate of the compound of Chemical Formula I may be used as an intermediate in the preparation of the compound of Chemical Formula I, or a pharmaceutically acceptable salt or a solvate thereof.

The compound of the Chemical Formula I according to the present invention includes not only pharmaceutically acceptable salts thereof, but also solvates and hydrates thereof which can be prepared therefrom. Stereoisomers of the compound represented by Chemical Formula I and intermediates thereof may be prepared in accordance with a conventional method.

In addition, the compound of Chemical Formula I according to the present invention may be prepared either in a crystalline form or in a non-crystalline form. When the compound of Chemical Formula I is prepared in a crystalline form, it may be optionally hydrated or solvated.

Moreover, the present invention provides an antiviral composition comprising, as an active ingredient, the compound of Chemical Formula I described above, or a pharmaceutically acceptable salt, a hydrate or a solvate thereof. In that case, the antiviral composition is particularly a composition for anti-Human Immunodeficiency Virus (HIV).

In Experimental Examples of the present invention, it was found that the compound represented by Chemical Formula I is an excellent substance, of which cytotoxicity is low, the effect of inhibiting HIV is excellent and physiological activity is high, and which exhibits safety in basic toxicity test result and has suitable solubility for drug properties.

The pharmaceutical composition according to the present invention may be formulated in an oral administration or an injection form. For example, a formulation for oral administration includes a tablet, a capsule and the like, and such formulation contains a diluent (for example, lactose, dextrose, sucrose, mannitol, sorbitol, cellulose and/or glycine) and a glidant (for example, silica, talc, stearic acid, or a magnesium or calcium salt of stearic acid, or polyethylene glycol), in addition to the active ingredient. The tablet may also contain a binder such as magnesium aluminum silicate, starch paste, gelatin, tragacanth, methyl cellulose, sodium carboxymethyl cellulose or polyvinyl picolidine, and depending on the case, it may contain a disintegrating agent such as starch, agar, alginic acid or a sodium salt thereof, or a boiling mixture and/or an absorbent, a colorant, a flavoring agent, and a sweeting agent. A formulation for injection is preferably an isotonic aqueous solution or suspension.

The above-mentioned composition may be sterilized and/or may contain an adjuvant such as a preservative, a stabilizer, a wettable powder or an emulsion accelerator, a salt for osmotic pressure adjustment and/or a buffer, and any other therapeutically useful substance.

The above-mentioned formulation may be prepared by a typical mixing, granulation or coating method, and may contain an active ingredient in the range of approximately 0.1 to 75% by weight, and preferably in the range of approximately 1 to 50% by weight. A unit formulation for a mammal of approximately 50 to 70 kg contains approximately 10 to 200 mg of an active ingredient.

The preferable dosage of the compound of the invention varies depending on the condition and the weight of patients, the progression of diseases, the form of drugs, the route and the time period of administration, but may be properly selected by those skilled in the art. The daily dose may be administrated via oral or parenteral routes in single or divided doses.

The pharmaceutical composition of the present invention may be administered to a mammal including a rat, a mouse, a domestic animal, a human and the like, through various routes. All routes of administration can be contemplated and it may be administered, for example, by oral, rectal, or intravenous, intramuscular, subcutaneous, intrauterine dural or intracerebroventricular injection.

Advantageous Effects

The compound represented by Chemical Formula I according to the present invention, a racemate or a stereoisomer thereof, or a pharmaceutically acceptable salt, a hydrate or a solvate thereof shows high selectivity and physiological activity against human immunodeficiency virus (HIV) with low toxicity, and thus is useful for the treatment of virus infection, in particular, human immunodeficiency virus (HIV) infection.

DETAILED DESCRIPTION OF EMBODIMENTS

Hereinafter, the present invention will be described in more detail with reference to the following preparation examples and examples. However, the following preparation examples and the examples are given for illustrative purposes only, and the scope of the present invention is not limited thereto.

Preparation Example 1: Preparation of 4-(chloromethyl)-1-methyl-1H-pyrazole hydrochloride Salt Dichloromethane(1.8 mL) and triethylamine (2 drops) were added to (1-methyl-1H-pyrazol-4-yl) methanol (380 mg, 3.39 mmol) prepared according to a known method (Frey, R. R,; et al, J. Med. Chem., 2008, 51, 3777-3787), and then resulting mixture was cooled to 0° C. A solution in which thionyl chloride (0.62 mL) was dissolved in toluene (1.8 mL) was slowly added thereto, and the mixture was stirred for 2 hours at 30° C. Solvent and excess amount of thionyl chloride were removed from reaction solution under reduced pressure to obtain a target compound. The compound was used in the next reaction without purification.

Preparation Example 2: Preparation of 4-(bromomethyl)-5-chloro-1,3-dimethyl-1H-pyrazole (5-Chloro-1,3-dimethyl)-1H-pyrazol-4-yl)methanol (937 mg, 5.8 mmol) prepared according to a known method (Attardo, G.; Tripthy, S., PCT Int. Appl. 2010, WO 2010-132999 A1) was dissolved in dichloromethane (40 mL) and then, cooled to 0° C. A solution in which phosphorus tribromide (0.54 mL, 5.8 mmol) was diluted with dichloromethane (5 mL) was slowly added thereto, and then resulting mixture was stirred for 1.5 hours at room temperature. Solvent was removed from reaction solution under reduced pressure to obtain a target compound. The compound was used in the next reaction without purification.

Example 1: (S)-2-(tert-butoxy)-2-(4-(4-chlorophenyl)-2,3,6-trimethyl-1 -((1 -methyl)-1 H-pyrazol-4-yl)methyl)-1 H-pyrrolo[2,3-b]pyridin-5-yl)acetic acid.

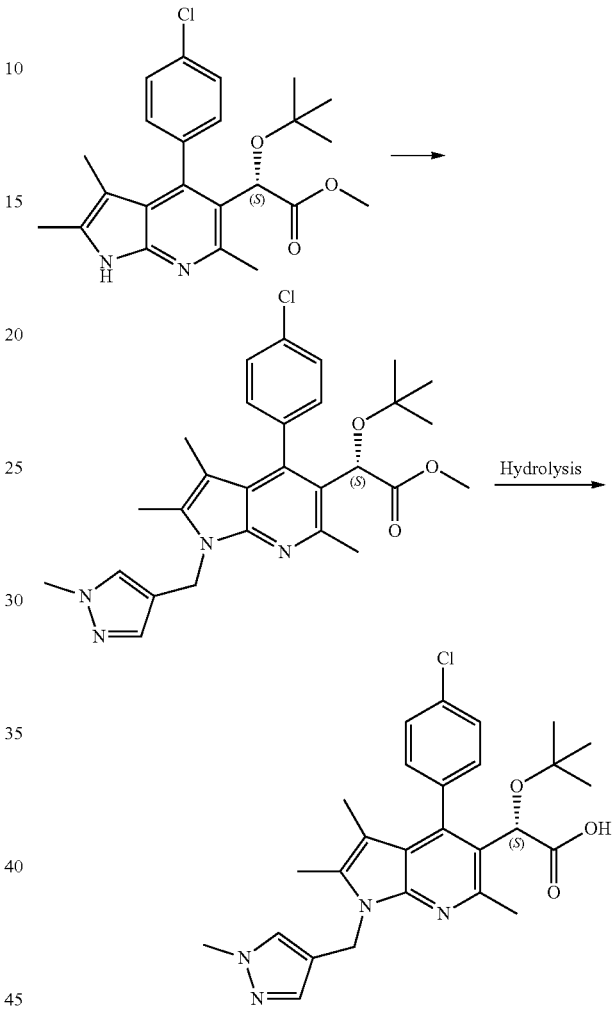

Step 1: Methyl(S)-2-(tert-butoxy)-2-(4-(4-chlorophenyl)-2,3,6-trimethyl-1H-pyrrolo[2,3-b]pyridin-5-yl)acetate (700 mg, 1.69 mmol) was dissolved in dimethylformamide (14 mL), and then cesium carbonate (2.75 g, 8.45 mmol) and 10 drops of triethylamine were added thereto. After temperature was adjusted to 40° C., the compound obtained in Preparation Example 1 (560 mg, 3.39 mmol) was added in portions thereto over 1 hour. Resulting mixture was stirred for 18 hours at the same temperature to complete the reaction. Reaction solution was cooled with an ice-water bath, and water (50 mL) was added thereto, and resultant was stirred for 10 minutes. The produced solids were filtered and washed with water. Without drying, the obtained solid was purified by silica gel column chromatography (eluent: ethyl acetate/n-hexane=1/2 and 1/1) to give a target compound (430 mg, 50%).

$^1$H-NMR(CDCl$_3$, 500 MHz) δ 1.01(s, 9H), 1.49(s, 3H), 2.30 (s, 3H), 2.75 (s, 3H), 3.69 (s, 3H), 3.83 (s, 3H), 5.11 (s, 1H), 5.32 (s, 2H), 7.30 (m, 2H), 7.44-7.47 (m, 4H); MS(EI, m/e)=509 (M$^+$).

Step 2: After the compound (369 mg, 0.724 mmol) obtained in Step 1 was dissolved in tetrahydrofuran (5.5 mL), 4N sodium hydroxide in methanol (0.98 mL) was added thereto, and resulting mixture was stirred for 18 hours at 35° C. Reaction solution was cooled to 10° C. and then neutralized by adding 4N hydrochloric acid. After solvent was removed from the reaction solution under reduced pressure, residue was purified by silica gel column chromatography (eluent: dichloromethane/methanol=95/5 and 90/10) to give a target compound (260 mg, 73%) in a white solid.

$^1$H-NMR(CD$_3$OD, 500 MHz) δ 1.00(s, 9H), 1.52 (s, 3H), 2.31 (s, 3H), 2.72 (s, 3H), 3.80 (s, 3H), 5.14 (s, 1H), 5.37 (bs, 2H) , 7.34-7.53 (m, 6H);

MS(EI, m/e)=495 (M$^+$).

Example 2: (S)-2-(tert-butoxy)-2-(1-((5-chloro-1,3-dimethyl-1H-pyrazol-4-yl)methyl)-4-(4-chlorophenyl)-2,3,6-trimethyl-1H-pyrrolo[2,3-b]pyridin-5-yl) acetic acid

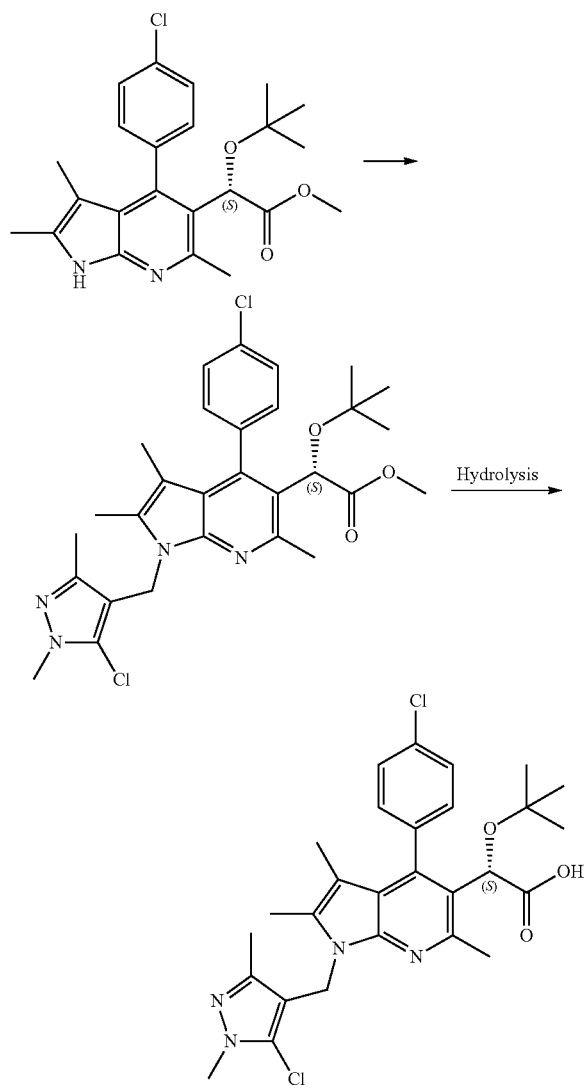

A target compound (30 mg, 44%) was obtained by reacting methyl(S)-2-(tert-butoxy)-2-(4-(4-chlorophenyl)-2,3,6-trimethyl-1H-pyrrolo[2,3-b]pyridin-5-yl)acetate (200 mg, 0.48 mmol) and the compound obtained in the Preparation Example 2 (432 mg, 1.44 mmol) in the same manner as in Example 1.

$^1$H-NMR(CD$_3$OD, 500 MHz) δ 1.00 (s, 9H), 1.49 (s, 3H), 1.90 (s, 3H), 2.19 (s, 3H), 2.68 (s, 3H), 3.75 (s, 3H), 5.20 (s, 1H) , 2.28 (dd, J=40.7, 15.8 Hz, 2H) , 7.24 (d, J=7.4 Hz, 1H), 7.47-7.39 (m, 2H), 7.63 (d, J=7.4 Hz, 1H);

MS (EI, m/e)=544 (M$^+$).

Experimental Example 1: Investigation of Inhibitory Effects Against HIV-1(Wild/Mutant Type) and Cytotoxicity Test of the Compound of the Invention In order to look into the HIV-1 (Wild/Mutant type) inhibition effects of the compound of the invention, a test for HIV-1 (Wild/Mutant type) inhibition effect was carried out in vitro as follows according to a known method (H. Tanaka et al., J. Med. Chem., 1991, 34, 349). MT-4 cells were used as host cells, and the degree of the compound of the present invention inhibiting cytotoxicity for the virus-infected MT-4 cells was investigated.

First, MT-4 cells were dispersed in a culture medium at a concentration of 1×10$^4$cells/well, and HIV-1 was inoculated so that the concentration was 500 TCI$_{50}$ (concentration at which 50% of the cells are infected)/well. Immediately after the inoculation, the cell dispersion was transferred in 100 μL each to a flat microtiter plate in which a sample of the compound of the invention was placed. The sample was incubated for approximately for 4 to 5 days at 17° C., and the virus inhibition effect was determined with an MTT method. In addition, the viability of experimentally infected cells was observed with MTT method to determine the degree of cytotoxicity. As a comparative compound, azidothymidine (AZT), Raltegravir, Dolutegravir, and Elvitegravir were used. The results are shown in Tables 1 and 2 below.

TABLE 1

| Compounds | Wild Type HIV-1(IIIB)in MT-4 Cells EC$_{50}$ (nM)* |
|---|---|
| Example 1 | 3.23 |
| Example 2 | 25.7 |
| Raltegravir | 5.85 |
| AZT | 2.24 |

*EC$_{50}$: concentration of 50% inhibition of HIV infection

TABLE 2

|  | NL4-3 wt IC$_{50}$(nM) | 4736_2* IC$_{50}$(nM) | 4736_4* IC$_{50}$(nM) | 8070_1* IC$_{50}$(nM) | 8070_2* IC$_{50}$(nM) | 1556_1* IC$_{50}$(nM) |
|---|---|---|---|---|---|---|
| Example 1 | 3.6 | 1.1 | 3.4 | 0.9 | 3.4 | 3.4 |
| AZT | 38.4 | 29.7 | 34.6 | 34.7 | 57.6 | 33.1 |
| Raltegravir | 4.6 | 351 | 351 | 4,322 | 3,844 | 3,757 |
| Dolutegravir | 3.2 | 3.5 | 3 | 8.5 | 4.4 | 3.2 |
| Elvitegravir | <0.10 | 410 | 320 | >10,000 | N/A | 276 |

*HIV-1 Clone: Raltegravir resistance mutants (4736_2/4736_4/8070_1/8070_2/1556_1)
** IC$_{50}$: The half maximal inhibitory concentration

Experimental Example 2: Pharmacokinetics Test of the Compound of the Invention Experiments were carried out to detect changes in in vivo kinetics including in vivo absorption, distribution, metabolism and excretion for the compound of Example 1 of the present invention. A tube was inserted into the jugular vein and femoral vein of a rat. A drug was administered into the femoral vein in the case of intravenous administration, and a drug was administered into the oral cavity in the case of oral administration. Blood was collected from the jugular vein at a predetermined time.

Dose concentration was 1 mg/kg for intravenous administration, and it was 2 mg/kg for oral administration. After centrifuging blood to separate plasma, the plasma and urine samples were pretreated with an appropriate organic solvent, and then concentration of the drug was analyzed with LC-MS/MS. From the data of the drug concentration in blood relative to time which were analyzed after oral and intravenous administrations, the noncompartmental pharmacokinetic parameter was calculated with WinNonlin (Pharsight, USA).

TABLE 3

Pharmacokinetic parameters in male rats

| Compound | Parameters | IV, 1 mg/kg | PO, 2 mg/kg |
|---|---|---|---|
| Compound of Example 1 | T$_{max}$ (hr) | — | 3.2 |
|  | C$_{max}$ (nM) | — | 914 |
|  | T$_{1/2}$ (hr) | 8.63 | 8.66 |
|  | AUC$_t$(hr*nM) | 6,081 | 8,734 |
|  | AUC$_\infty$(hr*nM) | 6,508 | 10,423 |
|  | CL (L/kg/hr) | 0.323 | — |
|  | V$_{ss}$ (L/kg) | 1.77 | — |
|  | F (%) |  | 71.8 |

Experimental Example 3: In Vitro Metabolic Stability Test of the Compound of the Invention The in vitro metabolic stability test was conducted for the compound of Example 1 of the present invention. In order to confirm in vitro metabolic stability, liver microsomal half-life of the compound was observed. A drug compound was reacted with NADPH using a species-specific (rat, dog, monkey, and human) liver microsome containing various metabolizing enzymes, and then half-life of the drug was determined by quantifying with LC-MS/MS in minutes. It was found that the compound of Example 1 was a stable compound with a half-life of 2 or 3 hours, or more.

TABLE 4

Liver microsomal stability (T$_{1/2}$, Min)

| Compounds | Rat liver (T$_{1/2}$, Min) | Dog liver (T$_{1/2}$, Min) | Monkey liver (T$_{1/2}$, Min) | Human liver (T$_{1/2}$, Min) |
|---|---|---|---|---|
| Compound of Example 1 | >145 | >145 | 133.3 | 135.9 |
| Control (Testosterone) | 0.7 | 23.6 | 13.0 | 19.7 |

Experimental Example 4: CYP450 Inhibition Test of the Compound of the Invention The CYP450 inhibition test was carried out for the compound of the present invention. To human liver microsomes (0.25 mg/ml), 0.1 M phosphate buffer (pH 7.4) and drug cocktails of five drug-metabolizing enzymes (CYP1A2, CYP2C9, CYP2D6, CYP3A4 and CYPC19) (Cocktail A: Phenacetin 50 μM, S-mephenytoin 100 μM, dextromethorphan 5 nM, midazolam 2.5 μM, Cocktail B: tolbutamide 100 μM), the compound of Example 1 was added at concentrations of 0 and 10 μM, respectively, and then cultured at 37° C. for 15 minutes. Subsequently, in order to terminate the reaction, an acetonitrile solution containing an internal standard (chloropropamide) was added thereto, and resulting mixture was centrifuged (14,000 rpm, 4° C.) for 5 minutes. Supernatant was then injected into LC/MS/MS system and the metabolites of the substrate drugs were simultaneously analyzed to thereby evaluate activities of the test compound inhibiting the drug-metabolizing enzymes. It has been evaluated that the compound of Example 1 does not exhibit an inhibitory activity against such five CYP enzymes.

TABLE 5

CYP inhibition (% of control activity) at 10 μM

| Compound | 1A2 | 2C9 | 2D6 | 3A4 | 2C19 |
|---|---|---|---|---|---|
| Compound of Example 1 | 113.6 | 68.5 | 101.6 | 92.1 | 101.6 |

Experimental Example 5: hERG K[30] Channel Assay of the Compound of the Invention hERG K+ channel assay was carried out to predict cardiotoxicity for the compound of the invention. The hERG activity of the compound was measured with HERG-HEK293 using automated planar patch clamp [PatchXpress 7000A]. This method is the most well-known method for studying ion channel, in which the flow of ions through the channel is directly measured with a voltage clamp. $IC_{50}$ value of hERG K+ channel for the compound of Example 1 was 66.7 μM. $IC_{50}$ value under 10 μM is a criterion for which it is determined to be possible to exhibit cardiotoxicity. Therefore, the compound of Example 1, of which the value was more than such criterion, was identified to be safe.

TABLE 6

| hERG K+ channel assay (Patch Clamp Recording Method) | |
|---|---|
| Compounds | $IC_{50}$(μM) |
| Compound of Example 1 | 66.7 |
| Control (Astemizole) | 0.079 |

The invention claimed is:

1. A compound represented by the following Chemical Formula I, a racemate or a stereoisomer thereof, or a pharmaceutically acceptable salt thereof:

Chemical Formula I

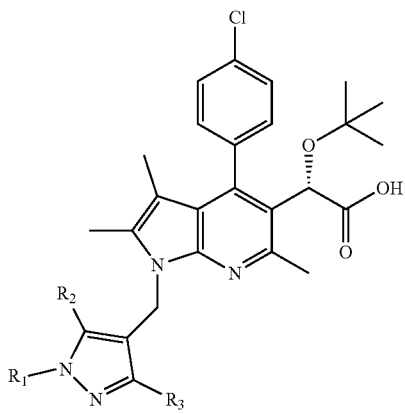

wherein:
$R_1$ is a $C_{1-6}$ alkyl, and
$R_2$ and $R_3$ are each independently hydrogen.

2. The compound, a racemate or a stereoisomer thereof, or a pharmaceutically acceptable salt thereof according to claim 1, wherein $R_1$ is methyl.

3. A method of treating a HIV infection comprising administering the compound of claim 1, a racemate, stereoisomer or pharmaceutically acceptable salt thereof, to a subject in need thereof.

* * * * *